US006420348B1

(12) United States Patent
Kim et al.

(10) Patent No.: US 6,420,348 B1
(45) Date of Patent: Jul. 16, 2002

(54) **PECTIC POLYSACCHARIDES PURIFIED FROM *ANGELICA GIGAS* NAKAI AND PURIFICATION METHOD AND USE AS IMMUNOSTIMULATING AGENT THEREOF**

(75) Inventors: Hwanmook Kim; Ikhwan Kim, both of Taejon; Sangbae Han, Choongcheongbuk-do; Kyungseop Ahn, Taejon; Namdoo Hong, Seoul, all of (KR)

(73) Assignees: Korea Institute of Science and Technology, Seoul; Hankook Sin Yak Pharm. Co. Ltd., Nonsan, both of (KR)

( * ) Notice: Subject to any disclaimer, the term of this patent is extended or adjusted under 35 U.S.C. 154(b) by 0 days.

(21) Appl. No.: 09/529,189

(22) PCT Filed: Oct. 9, 1998

(86) PCT No.: PCT/KR98/00310

§ 371 (c)(1),
(2), (4) Date: Sep. 8, 2000

(87) PCT Pub. No.: WO99/19365

PCT Pub. Date: Apr. 22, 1999

(30) Foreign Application Priority Data

Oct. 10, 1997 (KR) ............................................ 97-51930

(51) Int. Cl.$^7$ ............................ A61K 31/70; C07H 1/00
(52) U.S. Cl. ...................... 514/54; 536/123.1; 536/127
(58) Field of Search ............................... 536/123.1, 127; 514/54

(56) References Cited

FOREIGN PATENT DOCUMENTS

JP        3052820       *   3/1991

* cited by examiner

*Primary Examiner*—Elli Peselev
(74) *Attorney, Agent, or Firm*—Brian L. Buckwalter; Mathews, Collins, Shepherd & McKay, P.A.

(57) ABSTRACT

An acidic polysaccharide isolated from aqueous extracts of *Angelica gigas* Nakai roots is disclosed. The compound has both immunostimulatory and anti-neoplastic activity. The compound is comprised primarily of galacturonic acid, arabinose and galactose along with traces of xylose, rhamnose amd mannose. The molecular weight of the compound is about 10,000 Daltons.

7 Claims, No Drawings

PECTIC POLYSACCHARIDES PURIFIED FROM *ANGELICA GIGAS* NAKAI AND PURIFICATION METHOD AND USE AS IMMUNOSTIMULATING AGENT THEREOF

This Application is a 371 of PCT/KR98/00310 filed Oct. 9, 1998.

TECHNICAL FIELD

The present invention relates to a novel pectic substance and a purification method thereof. More particularly, the present invention relates to pectic polysaccharides isolated from *Angelica gigas* Nakai, which are immuno-stimulative, and a purification method thereof. Also, the present invention is concerned with use of the pectic polysaccharides in the treatment or prophylaxis of immune-related disease and in basic immunology research.

BACKGROUND ART

The immuno-stimulating agents derived from natural substances are used for the treatment of cancers, AIDS and chronically infected states by enhancing immunoresponses or restoring lowered immune functions. Extensive research on fungi, bacidiomycota and medicinal herbs has been made to obtain immuno-stimulating agent. Particularly, the polymer fractions of the natural substances showed immuno-stimulation, such as anticancer activity, anticomplementary activity, and induction of lymphocyte proliferation. Glucan polysaccharides, such as lentinan, PSK, and schzophyllan, derived mainly from mushrooms, are useful to be clinical usefulness in therapies of cancer.

It is reported in oriental medical documents that Angelica, belonging to family Umbelliferae, can be used for the treatment of gynecological diseases (anaemia, interruption in blood circulation, etc) by virtue of anodynic effect. From *Angelica gigas* Nakai, found only in Korea, coumarin substances, such as decursin, decursinol, nodakenetin, umbelliferon, nodakenin, and β-sitosterol, have been extracted, thus far.

Pharmaceutical research on the herb showed that the ether extract of *Angelica gigas* Nakai made the enucleated intestinal canals and uterus of rabbit excited. Free decursin and decursinol were reported to have a paralysis action on the enucleated intestinal canals of rabbit, a suppressive action on the enucleated heart of frog, and a breath-suppression and blood-depression action on rabbit. Recently, decursin have been found to have in vitro therapeutic activity against cancers and to enhance the activity of protein kinase C.

DISCLOSURE OF THE INVENTION

Bearing the above-mentioned situations in mind, the present inventors repeated thorough and intensive research with the aiming of finding a novel immuno-stimulating entity in *Angelica gigas* Nakai and finally, isolated a polysaccharide component which is immuno-stimulative and active against cancer.

Therefore, it is an object of the present invention to provide pectic polysaccharides which are immuno-stimulative and anticancer-effective.

It is another object of the present invention to provide a method for purifying the polysaccharides from *Angelica gigas* Nakai.

It is a further object of the present invention to provide information for use of the polysaccharides in the treatment or prophylaxis of cancers and immune-related diseases and in the recovery of immune functions.

It is still a further object of the present invention to provide information for use of angelan as an immuno-stimulating agent useful for basic immunology research.

In accordance with the present invention, the pectic polysaccharides which are purified by refluxing *Angelica gigas* Nakai in hot water and subjecting the hot water extract to ion exchange chromatography, are immuno-stimulative and shows anticancer activity.

BEST MODES FOR CARRYING OUT THE INVENTION

A detailed description will be given of a purification method of angelan, a pectic polysaccharide, from *Angelica gigas* Nakai and the physicochemical characteristics thereof, below.

Sliced roots of *Angelica gigas* Nakai were refluxed with hot water for 1 hr, followed by filtering the water through a four-folded gauze and Whatman filter paper. The filtrate was mixed with three volumes of ethanol and allowed to stand at 4° C. for 3 hours to give precipitates. They were obtained as brown polymers by centrifugation. From the fact that the polymers can easily obtained by ethanol precipitation and there are no denaturated protein precipitates even if solubilized precipitates in water are boiled for 20 min, the polymer fractions are assumed to contain a large amount of non-proteinous polymeric materials. Most of the colored material is absorbed in DEAE-cellulose, an anion exchange resin. Using the DEAE-cellulose absorption method, acidic and neutral fractions can be obtained. The acidic fraction was named angelan. They both are polysaccharides with a small amount of proteins. Angelan 10 KD in molecular weight was chemically characterized as a single substance as certified by the analytical high performance liquid chromatography method (HPLC).

Pectic polysaccharides compose most of the immuno-stimulating fraction of the hot water extract, amounting 85–90% of the total weight. The immuno-stimulating fraction also contains 7–8% of proteins and 15.5–68% of uronic acid. The fraction is also rich in calcium ion and magnesium ion in combination with other inorganic compounds including iron, aluminum, manganese, zinc, potassium, phosphorus, sulfur, etc.

Even after treatment with proteinase K, angelan has almost constant immune activity, showing that the immuno-stimulation principle of angelan resides in the polysaccharides alone or in combination with the inorganic compounds.

Quantitative and qualitative analyses for the sugars of angelan can be performed using thin layer chromatography (TLC) and ion exchange HPLC, respectively. The data demonstrate that the polysaccharides of angelan comprises galacturonic acid, galactose and arabinose as major components and mannose, rhamnose and xylose as minor components. That is, the composition of angelan, which consists mainly of galacturonic acid, arabinose and galactose, is typical of pectic polysaccharides which exist in a wide range of plants. Therefore, the major component of the immuno-stimulating principle of angelan is pectic polysaccharides and the immuno-stimulation of angelan is attributed to the pectic polysaccharides combined with the inorganic compounds. The immuno-stimulative polysaccharides isolated from *Angelica gigas* Nakai is 10 kDa or less in molecular weight.

Specific pathogen free mice for immune test were obtained from Korea Research Institute of Bioscience and Biotechnology, Korea. Investigation was done on the influence of angelan on the immune functions of the splenocytes including B cells, T cells and macrophages. Based on the data, the following conclusions were made.

The cellular targets in the angelan-induced immunopotentiation are divided into two types, i.e., direct and indirect targets. The direct exposure of angelan to splenocytes increases the expression of cytokines. The expression of IL-6, which is produced by activated macrophages, is enhanced by angelan. For IFN-γ, which is related to natural killer cells, a significant production increase can be induced by angelan. Also, IL-2 and IL-3, which are secreted from helper T cells, are expressed at an elevated level by angelan. However, the time-dependent analysis showed some differences in the onset time of angelan's action among the four cytokines. IL-6 and IFN-γ respond rapidly to angelan and the increased expression levels are maintained thereafter. In contrast, the production of IL-2 and IL-4 is weakly enhanced at delayed times. IL-2 production gradually increases and IL-4 production is affected for only a few hours after treatment with angelan. Accordingly, this suggests that macrophages and natural killer cells, which produce IL-6 and IFN-γ respectively, are primary cellular targets directly affected by angelan whereas helper T cells are indirectly affected by angelan.

Angelan has an direct influence on B cells. Similar to LPS, which is a B cell mitogen, angelan causes a high level of mitogenic proliferation of B cells. When total splenocyte populations including B cells, T cell and macrophages are treated with angelan, they are proliferated at a significant increased level. In the absence of T cells and macrophages, angelan also augments the proliferation of B cells whereas the B cell-depleted populations are not affected, which suggests that B cells are directly activated by angelan. Mitogenicity comparison of angelan with specific mitogens, i.e., lipopolysaccharide (LPS) as a B cell mitogen, phytohemagglutinin (PHA) and concanavalin A (Con A) as T cell mitogens, and pokeweed mitogen (PWM) as a comitogen, demonstrates that angelan behaves like LPS. That is, angelan is a B cell mitogen.

The immuno-stimulative effects examined above also provide information to use angelan as an immunostimulating agent or drug. As described above, angelan enhances the antibody production of B cells. The antibody production of B cells are accomplished in two routes: polyclonal activation of B cells to produce IgM independent on other cell types and T-dependent antibody response of B cells requiring T cells, macrophages and helper T cells. Angelan induces increased antibody production in the two antibody responses and particularly, augments T-dependent antibody response from the early time of treatment. Therefore, angelan is thought to influence B cells and macrophages at once.

To examine the anticancer activity of angelan, mice are transplanted with cancer cells. A test group which is treated with angelan shows a higher viability than non-treated groups. This anticancer activity of angelan comes from its immuno-stimulating activity. Mouse's immune functions stimulated by angelan defeat the cancer cells. Adriamicin, a typical anticancer chemical, is disadvantageous in that its high administration levels cause serious side effects with an insignificant therapeutic effect at low levels. According to the present invention, angelan can significantly reduce the administration dose of adriamicin with an improved anticancer effect, thereby preventing the side effects. In an in vivo experiment, co-administration of angelan and adriamicin at a dose of 0.3 mg/kg completely cured the mice affected with melanoma. In another experiment, angelan showed no cytotoxicity effect on cancer cells, implying that its anticancer effect comes from the enhancement in the immune defense rather than in cytotoxicity.

Using one or more pharmaceutically acceptable carriers, the angelan of the present invention may be formulated to pharmaceutical compositions in a routine manner. Suitable forms to be administrated via various routes, such as oral, rectal, subcutaneous, intravenous and intramuscular routes, include, for example, tablets, hard and soft gelatine capsules, liquor, emulsions, suspensions, suppositories, and ampules.

For the preparation of pharmaceutical compositions, angelan may be combined with therapeutically inactive inorganic or organic carriers. Lactose, corn starch or its derivatives, active stearic acid or its salts can be used as carriers for, e.g. capsules and hard gelatine capsules. Suitable carriers for soft gelatine capsules include, for example, vegetable oils, waxes, semi-solid and liquid polyols. If necessary, no carriers may be used. Examples of the carriers suitable to prepare liquor and syrups include water, alcohols, polyols, sucrose, invert sugars, and glucose. Examples of the carriers for ampules include water, polyols, glycerines and vegetable oils. For suppositories, natural and hardened oils, waxes, lipids, and semi-liquid polyols. In addition, the pharmaceutical composition of the present invention may contain preservatives, stabilizers, wetting agents, emulsifiers, sweetening agents, coloring agents, favors, osmosis-controlling salts, buffers, coating agents and/or antioxidants.

For the treatment of cancers, the angelan of the present invention may be administered at a wide range of dose. This administration dose may be adjusted according to personal conditions. In general, the pharmaceutically essential component of the composition may be daily administered at a dose of about 20 to 200 mg per kg of body weight for adults and preferably at about 30 mg. If necessary, the administration amount of angelan may exceed the upper limit. The daily dose may be administered at once or in installments unless the total amount is changed.

EXAMPLE I

Isolation of Angelan from *Angelica gigas* Nakai by Hot Water 300 g of crushed *Angelica gigas* Nakai root was added with 6 liters of water and refluxed at 100° C. for 1 hr. The extract was filtered through a four-folded gauze and then, through Whatman filter paper (No. 2). The filtrate was added with three volumes of ethanol and allowed to stand at 4° C. for 3 hours to give precipitates. They was obtained by centrifugation. For further purification, the precipitates were dissolved in water, added with three volumes of ethanol, and recovered by centrifugation. The precipitates were subjected to dialysis using MWCO 10,000. After the dialysis, the sample thus obtained was freeze-dried to give crude polysaccharides (4.6 wt % of dried sample). The crude polysaccharides were divided into an acidic fraction and a neutral fraction in the following manner. DEAE-cellulose resin carriers were immersed in a solution of the crude polysaccharides (4.6 g) in 200 ml of distilled water and allowed to stand for 2 hours with sporadic stirring, so as to absorb the polysaccharides. Before use, these carriers had been treated with an acid (i.e. 1M HCl) and an alkali (i.e. 1M NaOH), washed several times with distilled water and immersed in 50 mM Tris buffer (pH 7.0) for 30 min. At 2 hours after the absorption, the carriers were washed twice with the buffer and the polysaccharides were eluted from the carriers by using 10% NaCl solution. Addition of three volumes of ethanol to the eluted solution gave polysaccharide precipitates. After being harvested by centrifugation, the precipitates were dialyzed and freeze-dried to yield an acid polysaccharide, angelan.

EXAMPLE II
Composition of the Extract Fractions

The immuno-stimulating fractions from the hot water extract of *Angelica gigas* Nakai were measured for composition. The ethanol-extract fractions and the angelan fractions had a sugar content of 90% (w/w) and 85%, respectively, as measured by the phenol-sulfuric acid method. Using the Bradford method, all fractions were found to have a protein content of 7–8%. For uronic acid content, the Carbazole method was applied to the samples which were previously hydrolyzed with 2M trifluoroacetic acid (TFA). The angelan fractions were measured to be 68% in uronic acid content. Besides organic materials, various inorganic materials were found in the ethanol extract fractions. Ca and Mg ions were present at relatively large amounts (4.7% and 0.8%, respectively). Fe was contained at an amount of 3 mg/g, Al at 7.6 mg/g, Mn at 2.3 mg/g, and Zn at 0.25 mg/g. Trace elements included K, Na, P, S, Ti, Ba and Sr.

To investigate the constituting sugars of the samples, they were hydrolyzed with 2M TFA and subjected to thin layer chromatography (TLC) for qualitative analysis and ion exchange high performance liquid chromatography (HPLC) for quantitative analysis. The TLC using 60% acetonitrile as a running solvent showed that AG-1 fraction contained galacturonic acid, galactose, and arabinose at large amounts. Mannose, rhamnose and xylose were also detected although their amounts were small. The quantitative analysis data for the angelan fractions, obtained by ion exchange HPLC, are given in Table 1, below.

TABLE 1

Composition of Angelan-I and Angelan-II

| Constituents | | Angelan |
|---|---|---|
| Polysaccharides (molar ratio) | Arabinose | 3 |
| | Galactose | 8.3 |
| | Galacturonic acid | 14 |
| | Xylose | Trace |
| | Rhamnose | Trace |
| | Mannose | Trace |
| Organic materials (%) | Hexoses | 37.5 |
| | Uronic acid | 56.5 |
| | Proteins | 7.5 |
| Inorganic (trace) | Fe, Ca, Mg, Al, Mn, Zn, K, Na, P, S | |

As shown, the angelan fractions all contain galacturonic acid at large amounts with arabinose and galactose standing as minor sugars. This sugar composition is typical of the pectic substance which is ubiquitous in plants. Therefore, these data gave the information that the main components of *Angelica gigas* Nakai are polysaccharides of pectic substance.

In order to measure the molecular weights of the polysaccharides purified from *Angelica gigas* Nakai, gel permeation HPLC was performed using dextrans 10 KD, 40 KD, 70 KD, 500 KD and 2,000 KD in molecular weight as standards. Angelan was found to be not more than 10 KD in molecular weight.

EXAMPLE II
Effect of Extracts on T Cell Activity

The intermediate extracts and final extracts of the above examples were tested for immuno-stimulation. For this, there was taken advantage of a composite immune cell reaction method in which spleen cells were separated from two mice different in histocompatibility antigen and mixed with each other to induce an increase in the activity of T cells. Before being mixed, the cells were treated with the samples. After 3-day incubation, lymphocyte proliferation was measured by the incorporation of a radiolabeled base in the DNA synthesized. It was expressed as cpm per 250,000 cells. Results are given in Table 2, below. As apparent, all of the fractions have positive influence on the activity of T cells.

TABLE 2

Effect of Polysaccharide Fractions on T cells

| Samples | | Proliferation of T cell (cpm/250,000 cells) |
|---|---|---|
| Control (untreated) | | 6752 |
| Hot water extract | 25 µg/ml | 17705 |
| Ethanol extract | 25 µg/ml | 28087 |
| | 2.5 µg/ml | 12134 |
| | 0.25 µg/ml | 7854 |
| Angelan | 25 µg/ml | 22632 |
| | 2.5 µg/ml | 9622 |
| | 0.25 µg/ml | 7840 |

EXAMPLE IV
Proteolysis of the Extracts

To verify whether the immuno-stimulating principle of the extracts resides in proteins or other substances, the extracts were treated with proteases before being used for the test for the effect on T cell activity. As shown in Table 3, below, the immuno-stimulation effects of the polysaccharide extracts were constant irrespective of the treatment of protease K. These data show that the immuno-stimulating principle of the extracts does not come from proteins.

TABLE 3

Effect of the Proteolyzed Pectic Polysaccharides on T Cell Proliferation

| Samples | Proliferation of T cells (cpm/250,000 cells) |
|---|---|
| Untreated | 3424 |
| Ethanol Extract | 64472 |
| Ethanol Extract + Protease K | 63339 |
| Angelan | 57929 |
| Angelan + Protease K | 58664 |

EXAMPLE V

Effect of Angelan on Cytokine Production

Total splenocyte populations were cultured in the presence or absence of angelan (100 µg/ml). Total cellular RNA was extracted from the lymphocytes and then, subjected to quantitative RT-PCR. In this RT-PCR, IL-6 produced from macrophages, IFNγ produced from natural killer cells, IL-2 and IL-4, both secreted from helper T cells, were quantitated from the electrophoresis data of the PCR products. The results are given in Table 4, below.

TABLE 4

Cytokine Production

| Time (hrs) | IL-2 | IL-4 | IL-6 | IFN-γ |
|---|---|---|---|---|
| 0 | 0 | 0 | 0 | 1.041 |
| 4 | 0.731 | 1.055 | 19.038 | 3.245 |
| 24 | 1.051 | 0.325 | 19.869 | 3.163 |
| 48 | 1.639 | 0 | 18.777 | 2.383 |
| 72 | 2.351 | 0 | 12.849 | 2.529 |

As shown in the Table 4, IL-6 and IFNγ are strongly induced from the early time of treatment whereas the induction of IL-2 and IL-4 is weak. Thus, the data imply that angelan has direct influence on macrophages and natural killer cells from the treatment beginning. Although secreting IL-6 and IFNγ, helper T cells are thought to be indirectly affected by angelan at relatively late stages, from the low level of IL-2 and IL-4.

EXAMPLE VI
Effect of Angelan on Proliferation of Splenic Cells

Angelan was given to four kinds of cell preparations: a total spleen cell group including macrophage, B cell and T cell, a macrophage-depleted spleen cell group, macrophage/T cell-depleted spleen cell group, and a macrophage/B cell-depleted spleen cell group. After being treated with angelan at a dose of 1 to 100 μg/ml, the four groups were incubated for 3 days. The spleen cell proliferation was measured by the incorporation of a radiolabeled base into the cellular DNA synthesized. The results are given in Table 5, below.

TABLE 5

Effect of Angelan on Immune Cell Proliferation

| Angelan (μg/ml) | Proliferation (cpm/200,000 cells) | | | |
|---|---|---|---|---|
| | Φ/B/T | B/T | B | T |
| 3 | 21615 | 19069 | 28590 | 900 |
| 10 | 42843 | 37372 | 69512 | 1100 |
| 30 | 69583 | 77746 | 95603 | 1399 |
| 100 | 72574 | 90476 | 118859 | 1780 |

As shown in Table 5, angelan significantly increases the proliferation of the total and macrophage-depleted cell groups and more strongly increases that of the macrophage/T cell-depleted group, namely B cell-enriched group. However, angelan had no influence on the proliferation of the macrophage/B cell-depleted group, namely T cell-enriched group. This demonstrates that angelan allows selective induction of B cell to proliferation.

EXAMPLE VII
Mitogenic Patterns of Lymphocytes by Angelan

In this example, the action mode of angelan was compared with those of other lymphocyte mitogens in three different lymphocyte groups. Lipopolysaccharide (LPS) was employed to induce the proliferation of B cell while phytohemagglutinin (PHA) and concanavalin A (Con A) were used as T cell mitogens. As a comitogen, that is, in order to induce both T-cells and B-cells to proliferate, pokeweed mitogen (PWM) was used.

Angelan was given to three different cell groups: total cell group including T- and B-cells, T cell-depleted cell group, and B cell-depleted cell group. Each cell groups were treated with angelan or one of LPS, PWM, Con A and PHA. After incubation, lymphocyte proliferation was measured by the incorporation of 3H-thymidine into the cellular DNA. The results are given in Table 6, below.

TABLE 6

Comparison of Angelan and other Mitogens in Mitogenicity

| Mitogens | Proliferation (cpm/200,000 cells) | | |
|---|---|---|---|
| | B/T cells | B cells | T cells |
| Untreated | 230 | 264 | 824 |
| Angelan (100 μg/ml) | 9003 | 11162 | 681 |
| LFS (5 μg/ml) | 11665 | 11550 | 869 |
| Con A (5 μg/ml) | 6014 | 6566 | 3929 |
| PHA (5 μg/ml) | 1049 | 446 | 3127 |
| PWM (5 μg/ml) | 10212 | 358 | 12171 |

Similarly to the B cell-responsive mitogen (LPS), angelan, as shown in Table 6, effected mitogenicity on B cell-enriched groups, but not on T cell-enriched group. This demonstrates that angelan is selective for B cells. The total cell group was affected by angelan as well as the mitogens all. On the B cell-enriched group, angelan, LPS and PWM all had an effect, but Con A and PHA did not. The reverse phenomenon occurred on the T cell-enriched group.

EXAMPLE VIII
Effect on Antibody Production of B Cells

In this example, the effect of angelan on the antibody production of B cells was examined in two different assay systems. That is, advantage was taken of the fact that polyclonal activation of B cells to produce IgM does not depend on other cell types, but the T-dependent antibody response of B cells requires T cells and accessory cells such as macrophages. Spleen cells were activated with angelan. Thereafter, polyclonal antibody production of B cells was determined by Suspension Hemolytic assay and T-dependent antibody responses were also determined. For this, spleen cells were immunized with sheep red blood cells (SRBC) and/or angelan, followed by determining specific IgM response by Suspension Hemolytic assay. In this assay, the antibodies produced from the B cells destroyed the sheep red blood cells to release hemoglobins therefrom and the absorbance of hemoglobins was measured. Therefore, as the hemolysis occurs to a higher extent, the absorbance becomes larger. That is, the more the antibodies, the higher is the absorbance. The results are given in Table 7, below.

TABLE 7

Effect of Angelan on B cell Response

| Test Groups | Polyclonal Response | T-Dependent Response |
|---|---|---|
| Untreated group | 0 | 0 |
| Angelan-treated Group | | |
| 1 μg/ml | 0 | 0.323 |
| 3 μg/ml | 0 | 0.333 |
| 10 μg/ml | 0.001 | 0.680 |
| 30 μg/ml | 0.132 | 0.951 |
| 100 μg/ml | 0.220 | 1.271 |
| | | 0.984 |

As shown in Table 7, angelan itself was able to polyclonally activate B cells into antibody producing cells from 30 μg/ml. The same concentration of angelan also potentiated the T-dependent antibody response and the sensitivity was relatively high compared to polyclonal activation of B cells. The significant increase of antibody production was observed from 3 µg/ml of angelan in the T-dependent antibody response and, in the polyclonal activation of B cells, it was observed at 30 and 100 µg/ml. From the increase of the sensitivity in the T-dependent antibody response, angelan was assumed to have weak influence on B cells alone, but strong influence on macrophages and helper T cells.

EXAMPLE IX

Effect of Angelan on in vivo Immune Functions

Mice were immunized by intraperitoneal injection of sheep red blood cells and angelan was injected intraperitoneally. After 4 days, spleen cells were isolated and the number of antibody producing cells was enumerated by plaque forming cell assay. The results are given in Table 8, below.

TABLE 8 in vivo Immuno-Stimulation Angelan

| Test Groups | No. Of Ab-Producing Cells (/$10^6$ cells) |
|---|---|
| Untreated | 60 |
| SRBC | 981 |
| SRBC + Angelan-I | 3126 |
| SRBC + Angelan-II | 2020 |

As shown in Table 8, the greater number of antibodies from the angelan-treated animals demonstrates that angelan potentiates the immune functions.

EXAMPLE X

Anticancer Effect of Angelan

Because of serious side-effects of anticancer chemicals, immuno-stimulating agents attract much attention and have been continually developed. Use of immuno-stimulating agents in anticancer therapy brings about a significant improvement in therapeutic effect as well as reduces the side effects of chemicals. Whether the angelan's in vivo and in vitro immuno-stimulation, as evident in the above examples, could be developed to anticancer activity, was examined in this example.

The host resistance model to syngeneic tumors was prepared by the intraperitoneal transplantation of B16F10 melanoma to BDF1 mice. After transplantation, angelan was administered at a dose of 100 mg/kg/day while adriamicin was administered at a dose of 0.1 to 0.3 mg/kg. The survival rates of the treated mice was based on the viability of non-treated mice, and the number of the animals which survived for 60 days after the implantation, was counted. The results are given in Table 9, below.

TABLE 9

Anticancer Activity of Angelan

| Test Groups | Viability (%) | Survival Animals (10 in total) |
|---|---|---|
| Untreated | 100 | 0 |
| Angelan alone | >220 | 3 |
| Adriamicin 0.1 (mg/kg) | 195 | 0 |
| Adriamicin 0.1 + Angelan | >274 | 6 |
| Adriamicin 0.3 (mg/kg) | >240 | 2 |
| Adriamicin 0.3 + Angelan | >330 | 10 |

As shown in Table 9, administration of angelan alone or in combination with the anticancer chemical increased the therapeutic effect against cancers. Particularly, co-administration of angelan and adriamicin at a dose of 0.3 mg/kg completely cured the cancer.

In order to examine the toxicity of angelan, the body weights of the mice were measured during the treatment with angelan. There were observed no weight loss. Thus, angelan is of no toxicity. The improved therapeutic effect by use of the chemical at such a low amount as not to cause toxicity with the aid of the immuno-stimulator, is a great advance in anticancer therapy.

EXAMPLE XI

Direct Cytotoxicity Effect of Angelan on Cancer Cells

Whether the anticancer effect of angelan came from specific mediation by cytotoxic T cells or from nonspecific mediation by macrophages and natural killer cells, was proven as follows. B16F10 cancer cells were treated with angelan and adriamicin at a dose of 0.3 to 30 µg/ml. After incubation for 2 days, the number of the survived cells was countered. The survival number of the treated cells was expressed as a ratio compared with the number of the non-treated cells. The results are given in Table 10, below.

TABLE 10

Direct Cytotoxicity of Angelan

| Test Groups | Adriamicin | Angelan |
|---|---|---|
| Untreated | 100 | 100 |
| 0.3 µg/ml | 56 | 100 |
| 1 µg/ml | 29 | 96 |
| 3 µg/ml | 9 | 97 |
| 10 µg/ml | 0 | 96 |
| 30 µg/ml | 0 | 95 |

Adriamicin showed cytotoxicity on cancer cells, proving itself as a cytotoxicity-mediated anticancer agent. In contrast, angelan had no cytotoxicity effect on cancer cells, implying that its anticancer effect comes from the enhancement in the immune defense rather than in cytotoxicity.

INDUSTRIAL APPLICABILITY

As apparent from the data of Examples, the angelan purified according to the method of the present invention can be used as an active agent against cancer and an immuno-stimulative. The immuno-stimulating composition containing galacturonic acid, arabinose, and galactose can be useful as a drug for the treatment and prophylaxis of the immune-related diseases including cancers and as a sample for basic immunology research.

What is claimed is:

1. A purified immunostimulating anticancer acidic polysaccharide compound from *Angelica gigas* Nakai having the following properties:

i) a sugar content of from at least about 85% to about 90%;

ii) a composition comprising about 56% uronic acid, 37% hexoses and 7% proteins;

iii) a saccharide composition after hydrolysis with 2M trifluoroacetic acid comprising galacturonic acid, arabinose and galactose in a ratio of about 14:3:8.3 and traces of xylose, rhamnose and mannose iv) a molecular weight of about 10 kiloDaltons.

2. A method for the production of a purified acidic polysaccharide compound from *Angelica gigas* Nakai of claim 1 comprising:

i) preparing an aqueous extract of sliced roots of *Angelica gigas* Nakai by refluxing the roots in water and filtering the undissolved solids;

ii) adding ethanol to the filtrate, cooling and recovering a first precipitate;

iii) dissolving said first precipitate in water, dialyzing the filtrate and freeze-drying the resulting aqueous solution to produce a first polysaccharide fraction;

iv) dissolving said first polysaccharide fraction in water and stirring with an DEAE-cellulose resin to absorb the acidic polysaccharides;

v) washing the resin with water and eluting the absorbed product with a 10% NaCl solution;

vi) precipitating a second polysaccharide fraction with ethanol and isolating said second polysaccharide fraction;

vii) dialyzing the an aqueous solution of said second polysaccharide fraction to remove inorganic salts and freeze-dying the resulting solution.

3. A purified immunostimulating anticancer acidic polysaccharide compound from *Angelica gigas* Nakai prepared in accordance with the method of claim 2.

4. A method for treating melanoma in mammals comprising administering to the mammals in need of such treatment an effective amount of a compound of claim 1.

5. A method for treating melanoma in mammals comprising administering to the mammals in need of such treatment an effective amount of a compound of claim 3.

6. A method for enhancing immune response in mammals comprising administering to the mammals in need of such treatment an effective amount of a compound of claim 1.

7. A method for enhancing immune response in mammals comprising administering to the mammals in need of such treatment an effective amount of a compound of claim 3.

* * * * *